United States Patent [19]

Viola et al.

[11] Patent Number: 5,522,534
[45] Date of Patent: Jun. 4, 1996

[54] ANVIL FOR SURGICAL STAPLER

[75] Inventors: Frank J. Viola, Sandy Hook; Phillip D. Calabrese, Danbury, both of Conn.

[73] Assignee: United States Surgical Corporation, Norwalk, Conn.

[21] Appl. No.: 130,203

[22] Filed: Oct. 1, 1993

[51] Int. Cl.$^6$ ............................................. A61B 17/115
[52] U.S. Cl. .................. 227/179.1; 227/19; 227/175.1
[58] Field of Search ........................ 227/179, 19, 175, 227/175.1, 179.1

[56] References Cited

U.S. PATENT DOCUMENTS

| | | |
|---|---|---|
| D. 271,994 | 12/1983 | Noiles et al. . |
| D. 273,041 | 3/1984 | Noiles et al. . |
| 4,304,236 | 12/1981 | Conta et al. . |
| 4,319,576 | 3/1982 | Rothfuss . |
| 4,351,466 | 9/1982 | Noiles . |
| 4,473,077 | 9/1984 | Noiles et al. . |
| 4,488,523 | 12/1984 | Shichman . |
| 4,573,468 | 3/1986 | Conta e al. . |
| 4,603,693 | 8/1986 | Conta et al. . |
| 4,606,343 | 8/1986 | Conta et al. . |
| 4,646,745 | 3/1987 | Noiles . |
| 4,700,703 | 10/1987 | Resnick et al. . |
| 4,903,697 | 2/1990 | Resnick et al. . |
| 5,005,749 | 4/1991 | Aranyi . |
| 5,122,156 | 6/1992 | Granger et al. . |

FOREIGN PATENT DOCUMENTS 2070499  9/1981  United Kingdom .

OTHER PUBLICATIONS

"Information Bookelt for an Auto Suture, Surgical Stapling Instrument", United States Surgical Corporation, copyright 1984.

Primary Examiner—Rinaldi I. Rada

[57] ABSTRACT

An anvil assembly for use with a circular surgical stapling device having a housing and venting means, in the form of vent holes, for venting the interior of the anvil assembly. The housing includes channeling means in the form of a plurality of longitudinally extending and radially spaced surface grooves in an outer surface of the housing which are communicable with the vent holes to aid in directing a flow of air between the vent holes and the outer surface of the housing member to significantly reduce a suction effect therebetween. The channeling means further allows extruded tissue and debris to flow freely from the vent holes.

14 Claims, 4 Drawing Sheets

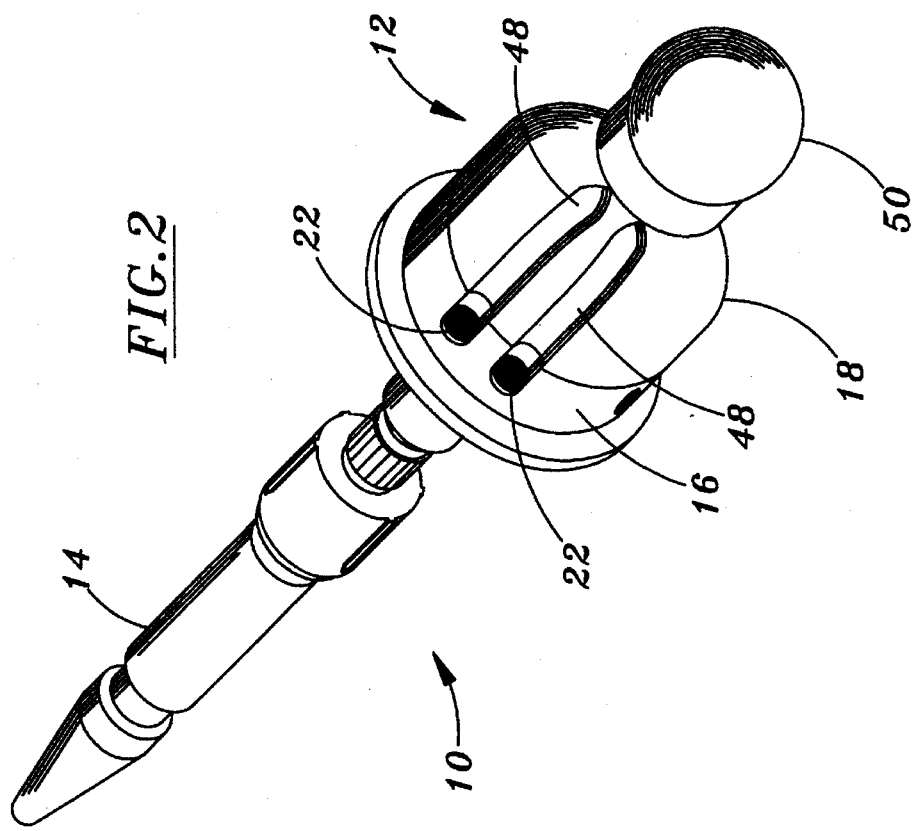
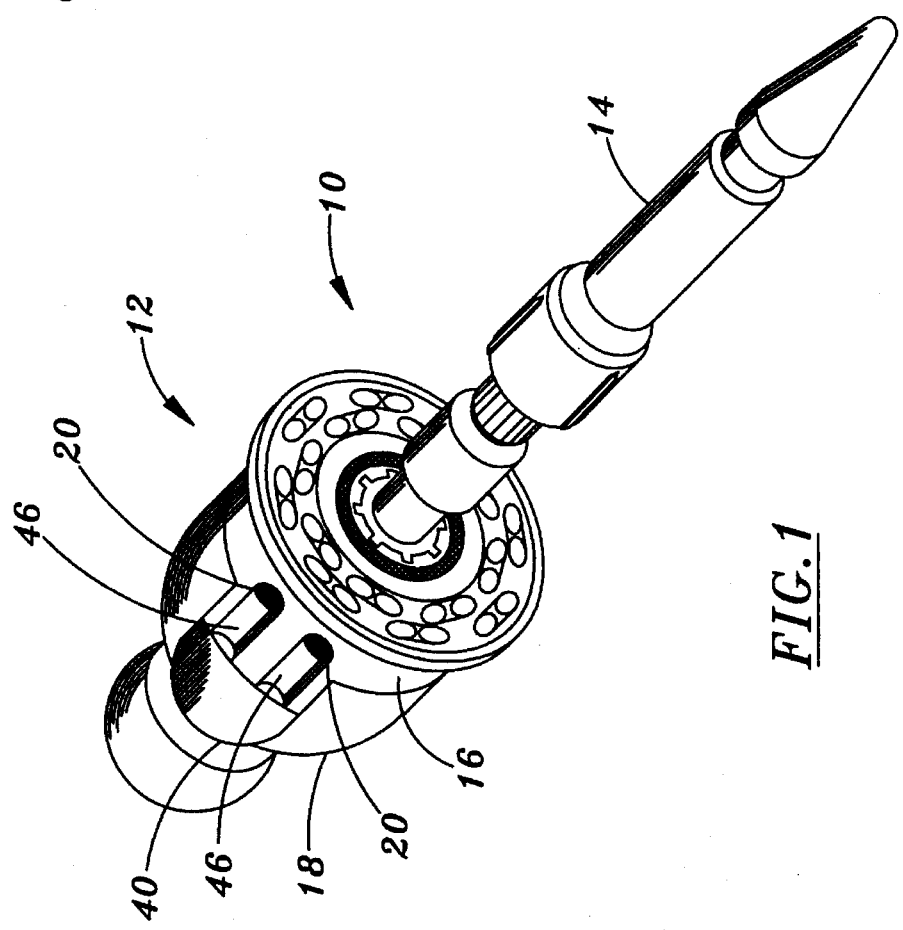

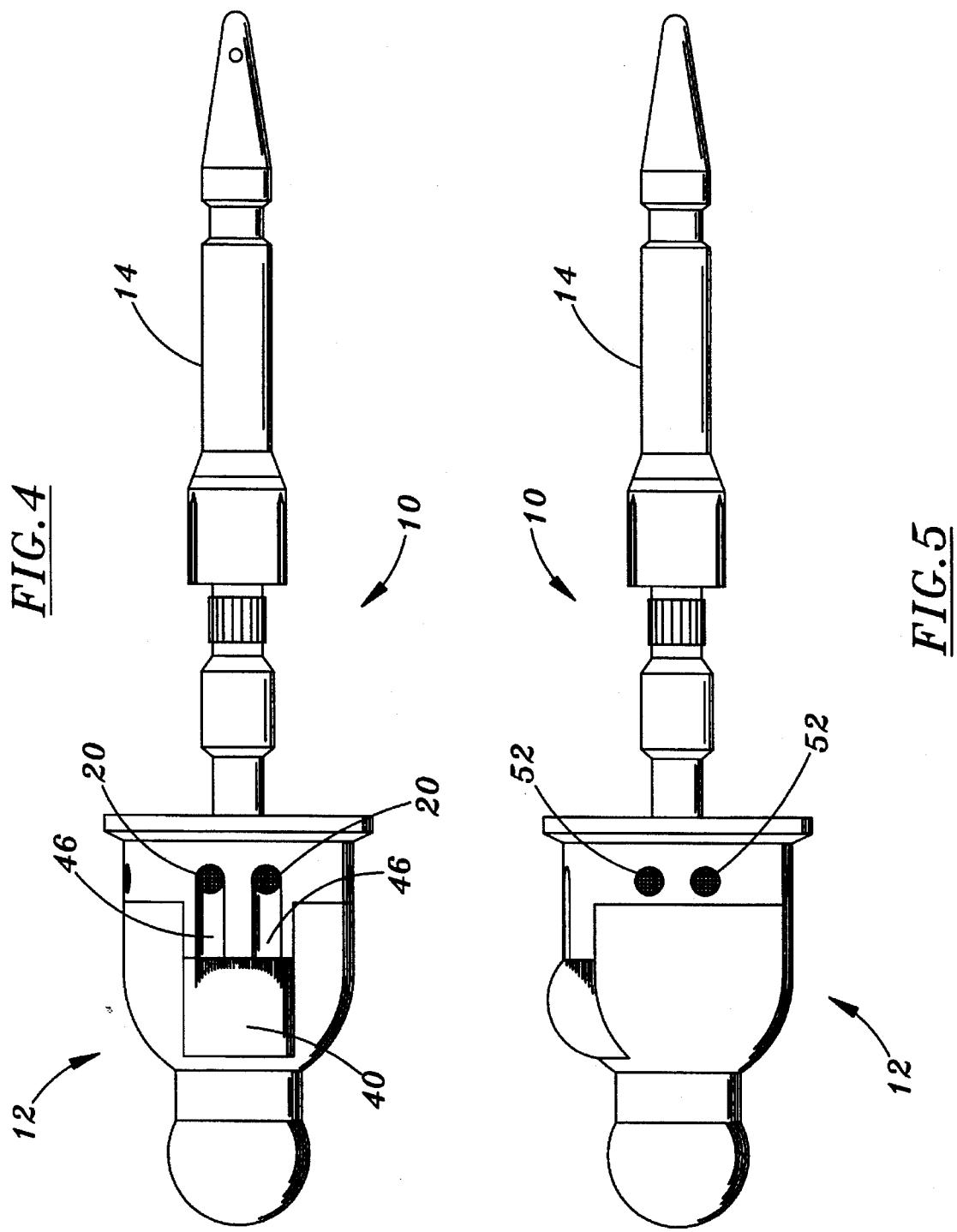

ANVIL FOR SURGICAL STAPLER

BACKGROUND OF THE INVENTION

1. Field of the Invention

This invention relates to a surgical stapling instrument for joining hollow body organs and more particularly to a vented anvil assembly having channels for facilitating flow of gas, tissue and other debris between outer and inner surfaces of the anvil assembly during use.

2. Description of the Prior Art

Heretofore, it has been known to use surgical staplers to connect hollow body organs. Typically, the stapling device consists of a handle portion, an elongated portion, a staple carrying portion, and an anvil carrying portion. In use, the anvil carrying portion is positioned in one hollow body organ and the stapling carrying portion of the instrument is positioned in a second hollow body organ. The anvil carrying portion is then attached to the staple carrying portion and retracted towards the staple carrying portion, thereby drawing the two hollow body organs together into an abutting relationship. As the tissue sections are drawn together, air, tissue and other debris are usually trapped and compressed in the confined space between the staple carrying portion and the anvil carrying portion. This can result in undesirable pressure build up in the space between the anvil and staple carrier, which can interfere with the anastomosis.

When the tissue is sufficiently drawn or clamped together, the instrument is fired to eject the staples from the staple carrying portion. The staples pass through the clamped tissue sections and are formed against the anvil carrying portion thereby securing the tissue sections together. Subsequently, a circular knife member is advanced through excess tissue and into a knife abutment ring on the anvil. Movement of the knife within the confined space between the staple carrying portion and the anvil carrying portion further reduces the volume of space in which excess tissue fluid and other debris are trapped. Because tissue and fluids are relatively incompressible, this additional reduction in volume can also create high pressures and tissue trauma in the confined space.

To relieve this undesirable increase in pressure in the confined space, several instruments have been provided with venting means, in the form of vent holes, in the anvil and staple carrying portions leading outward from the enclosed space. Examples of such venting means can be found in commonly assigned U.S. Pat. Nos. 4,606,343; 4,603,693; and 4,573,468 to Conta et al.; and 4,351,466 to Noiles. It has been observed that without the vent holes there is a tendency for the tissue to extrude outward between the clamped faces of the staple carrying portion and the anvil carrying portion. In instruments having vent holes in the anvil portion, it is common to find tissue in significant quantity extruded into and through these vent holes. In some instances, the excess tissue and other debris extruded through the vent holes may plug the vent holes due to the proximity of the adjacent hollow organ tissue section.

While the aforementioned devices generously vent the interior of the stapling mechanism to prevent the buildup of excess pressure in the confined space within the stapling mechanism, if the vent holes are blocked by tissue and other debris, a suction effect between the adjacent hollow body tissue section and the anvil can occur when the instrument is withdrawn from the body. This suction effect is undesirable during removal of the stapler. Thus, there exists a need to reduce the suction effect between an outer surface of the anvil portion and the surrounding tissue sections during removal of the anvil from the tissue section and to reduce blockage of the vent holes by extruded tissue and other debris.

SUMMARY OF THE INVENTION

The present invention is directed to a circular stapling instrument of the type described hereinabove and more particularly to a vented anvil assembly for use with the circular surgical stapling instrument. Specifically, there is provided a detachable anvil assembly having means for aiding removal of the anvil assembly from a tubular organ. The anvil assembly includes means for reducing surface attraction between an outer surface of an anvil housing and an inner surface of a hollow organ tissue section upon removal of the anvil assembly.

The attraction reducing means generally consists of the aforementioned venting means, which includes holes extending from an inner surface of the anvil housing to an outer surface of the anvil housing, and further includes surface depressions or grooves communicable with the vent holes and which preferably extend distally over the outer surface of the anvil housing. It has been found that the particular configuration of longitudinally extending grooves significantly decreases the suction effect between the outer surface of the anvil housing, and associated vent holes, and the surrounding inner surface of the hollow organ tissue section. The grooves further aid in channeling excess extruded tissue and other debris away from the vent holes, thereby permitting suction reducing flow to pass through the anvil.

Thus, it is an object of the present invention to provide an anvil assembly for use with a circular surgical stapler wherein the anvil assembly has channeling means to direct the flow of air tissue and debris between an outer surface of an anvil housing and a surrounding tissue section to reduce the potential for suction effects and tissue buildup therebetween.

DESCRIPTION OF THE DRAWINGS

A preferred embodiment of the invention is described hereinbelow with reference to the drawings wherein:

FIG. 1 is a perspective view of the invention showing grooves extending from the vent holes to a lock button;

FIG. 2 is a perspective view of the invention showing grooves extending from a pair of vent holes distally towards the tip of the anvil housing;

FIG. 4 is a side plan view of the invention showing the grooves illustrated in FIG. 1;

FIG. 5 is a side plan view of the invention showing vent holes on a side of the anvil housing.

DETAILED DESCRIPTION OF THE INVENTION

Figure 3:
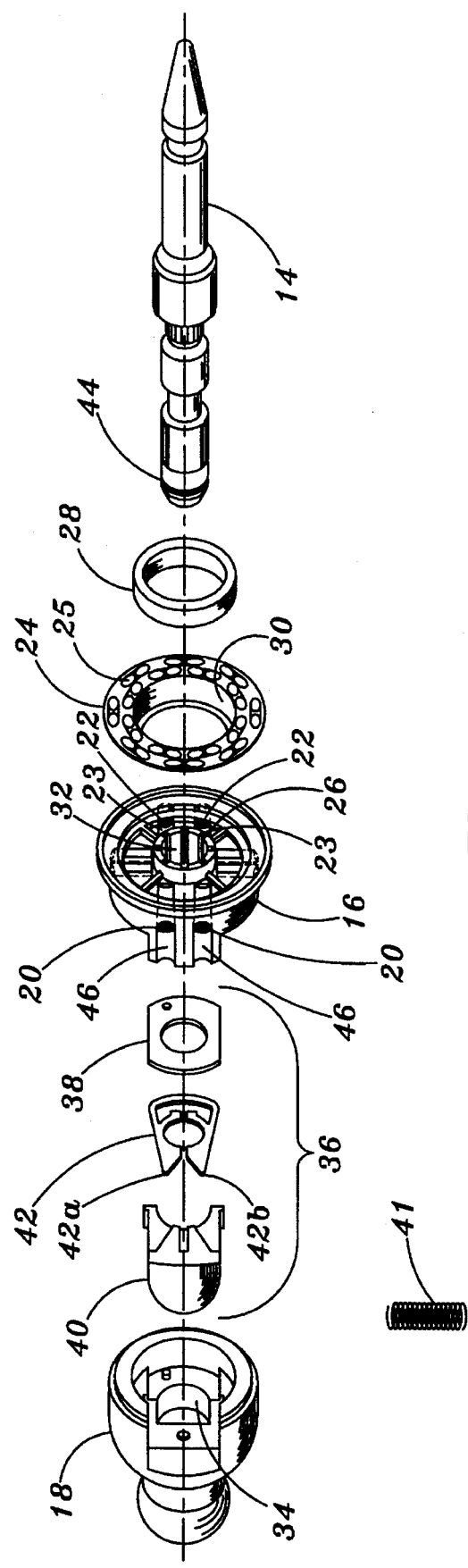
FIG. 3 is an exploded perspective view of the invention.

Referring now to FIGS. 1–6 wherein like reference numerals indicate like parts and more particularly with reference to FIG. 1, it can be seen that the vented anvil assembly 10 consists generally of an anvil carrying housing 12 and an elongated center rod 14. Anvil housing 12 includes proximal cap portion 16 and a distal cap portion 18.

As can best be seen in FIGS. 1 and 2 proximal cap portion 16 is provided with vent holes 20 and 22 formed in an outer surface thereof and extending into inner anvil surface 26. Vent holes 20 and 22 extend towards and communicate with slots 23 formed in inner anvil surface 26 (see FIG. 3), in a manner similar to that disclosed in U.S. Pat. No. 4,304,236 to Conta et al., the disclosure of which is incorporated by reference herein.

Referring now to FIG. 3, it can be seen that cap portion 16 houses a staple anvil ring 24, having staple forming cups or buckets 25 which form fastener clinching means, which is positionable within an inner anvil surface 26 of cap portion 16. Additionally, knife abutment ring 28 is inserted in a center area 30 of staple anvil ring 24.

Center rod 14 is longitudinally insertable through bore 32 in cap portion 16 and extends into bore area 34 of distal cap portion 18. Center rod 14 is held in place in distal cap portion 18 by means of lock mechanism 36 which consists of backing plate 38, button 40 and snap ring 42. Button 40 is slidably disposed within a slot 39 formed in distal cap portion 18 and biased outwardly by spring 41 positioned in bore area 34. Snap ring 42 is dimensioned to receive groove 44 on center rod 14 and serves to hold center rod 14 in place on anvil housing 12. By pushing button 40 radially inward, snap ring 42 is cammed open by forcing legs 42a and 42b outwardly, thereby allowing center rod 14 to be removed from anvil housing 12.

As can best be seen in FIGS. 1, 3 and 4, channeling means, in the form of a pair of radially spaced surface grooves 46, are formed in cap portion 16 which extend distally from vent holes 20. Grooves 46 terminate against button 40 and form surface depressions in an outer surface of anvil housing 12.

Similarly, as best seen in FIG. 2, the channeling means further includes a second pair of radially spaced surface grooves 48 formed in anvil housing 12 which are communicable with vent holes 22. Grooves 48 extend distally from vent holes 22 in proximal cap portion 16 across distal cap portion 18 to the base of anvil housing knob 50. With reference to FIG. 3, vent holes 22 communicate with slots 23 in inner housing surface 26. Similar slots are provided to communicate with other vent holes. Surface grooves 46 and 48 are preferably located on opposite sides of anvil housing 12, i.e. radially spaced by 180°. As shown in FIG. 5, additional vent holes 52 may be provided on cap portion 16 of anvil housing 12.

Figure 6:
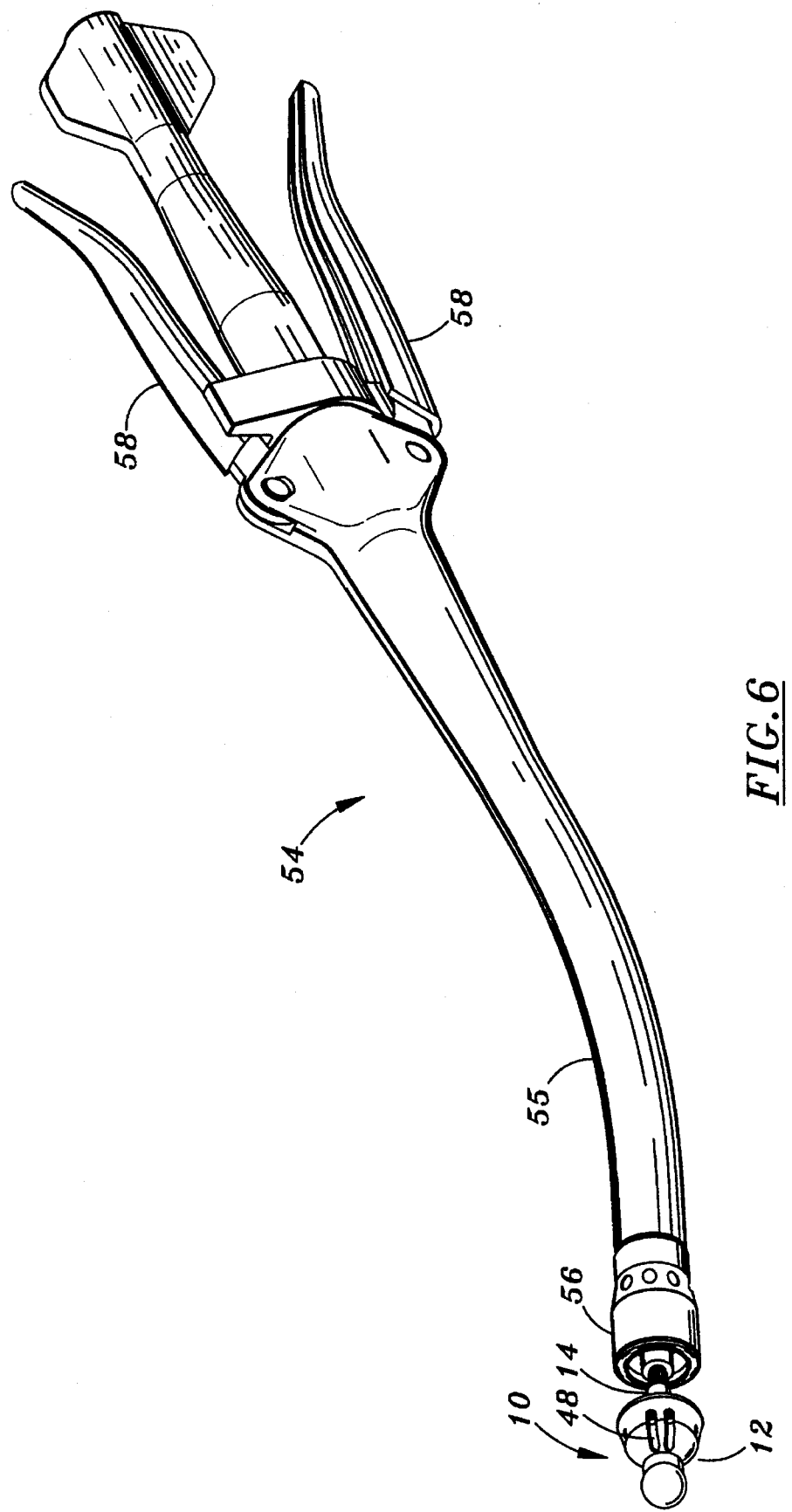
FIG. 6 is a perspective view of a circular surgical stapling device for use with the anvil assembly.

In use, portions of a circular surgical stapler are inserted into first and second hollow body organ sections as described above. A stapler 54 suitable for use with vented anvil 10 is shown in FIG. 6. Stapler 54 includes an elongated portion 55, staple carrying portion 56 and handles 58. Vented anvil 10 may be detachable from stapler 54 to facilitate installation within a hollow body organ section. Initially, vented anvil 10 is positioned within a first hollow body organ and stapler 54 is positioned within a second hollow body organ. The first and second hollow body organs are typically purse stringed after which vented anvil 10 is connected to stapler 54 by means of center rod 14. Vented anvil 10 is then retracted towards staple carrying portion 56, thereby drawing the first and second hollow body organs together into an abutting relationship. As vented anvil 10 is retracted towards staple carrying portion 56 of stapler 54, air, tissue and other debris are compressed therebetween causing a build-up of pressure which can be reduced by flow through the anvil's vent holes. Handles 58 of stapler 54 are then pivoted closed to drive staples located in staple carrying portion 56 through the first and second hollow body organs and into anvil buckets 25 to crimp the staples about the organs.

Once the tissue sections have been stapled together a knife blade is advanced through the organs and against knife abutment ring 28 to cut excess tissue. Vented anvil 10 is then extended away from staple carrying portion 56 to release the stapled hollow body organs. The surgical instrument, including the vented anvil 10, is then withdrawn from the body. During the withdrawal of vented anvil 10, a pressure differential can build between the interior of the anvil housing 12 and the space within the hollow body organ located distally of the vented anvil 10. This pressure differential may cause an attraction, or suction effect, between an outer surface of vented anvil 10 and the surrounding hollow organ tissue section. Vent holes 20, 22 and 52 and surface channeling grooves 46 and 48 aid in reducing this pressure differential and the associated suction effect, by allowing air, tissue and other debris to flow freely between the tissue section and anvil housing 12.

Additionally, as noted above, excess tissue and debris may be extruded out through vent holes 20, 22 and 52 as the tissue sections are clamped together, thereby blocking or "plugging" vent holes 20, 22 and 52. By extending grooves 46 and 48 from vent holes 20 and 22, extruded tissue and debris are directed away from vent holes 20 and 22 thereby aiding flow through the holes. In this manner, surface channeling grooves 46 and 48 substantially aid in the withdrawal of the anvil assembly.

While the above described invention has been shown to include surface channeling grooves in the anvil housing, it may be noted that numerous shapes and forms of surface depressions in the anvil head which are communicable with venting means will suffice to channel air, tissue and other debris between the vent holes and surrounding tissue sections to accomplish a reduction of the suction effect and associated trauma between the anvil housing and the surrounding tissue sections. It is also within the scope of the invention to provide ridges or projections rather than depressions or grooves to direct air flow and the debris between an outer surface of the anvil housing and a surrounding tissue sections.

While the invention has been particularly shown and described with reference to the preferred embodiments, it will be understood by those skilled in the art that the various modifications and changes in form and detail may be made therein without departing from the scope and spirit of the invention. Accordingly, modifications such as those suggested above, but not limited thereto, are to be considered within the scope of the invention.

What is claimed is:

1. An anvil assembly for use with a surgical fastening device comprising:

a) a shaft having first and second ends and mounting means for mounting to the surgical fastening device;

b) an anvil member mounted on said shaft at said second end, said anvil member having a housing and an array of fastener clinching means disposed thereon;

c) means associated with said housing for venting of gaseous pressure, tissue or debris from within said housing; and d) means formed on an outer surface of said housing and communicable with said venting means for channeling the passage of air, tissue or debris between said outer surface of said housing and a surrounding tissue section, said channeling means including at least and elongated surface depression formed on said outer surface.

2. The anvil assembly as recited in claim 1 wherein said at least one elongated surface depression is at least one longitudinally extending groove formed on said outer surface of said housing.

3. The anvil assembly as recited in claim 1 wherein said at least one elongated surface depression is a plurality of radially spaced grooves formed on said outer surface of said housing.

4. The anvil assembly as recited in claim 3 wherein said grooves are radially spaced apart approximately 180°.

5. The anvil assembly as recited in claim 1 further comprising means disposed on said shaft for detachably removing said anvil member from said shaft.

6. The anvil assembly as recited in claim 1 wherein said at least one elongated surface depression is a first and a second longitudinally extending groove, said first and second grooves being of substantially unequal dimensions.

7. The anvil assembly as recited in claim 6 wherein said first and second grooves are of substantially unequal length.

8. The anvil assembly as recited in claim 1 wherein said channeling means includes a plurality of surface depressions.

9. The anvil assembly as recited in claim 8 wherein said plurality of surface depressions are of substantially similar dimensions.

10. The anvil assembly as recited in claim 1 wherein said venting means includes a vent hole extending between an interior of said anvil assembly and said outer surface of said housing.

11. A circular surgical stapler comprising:
 a) a frame portion;
 b) a staple carrying portion containing an annular array of surgical staples, said staple carrying portion mounted on a distal end of said frame;
 c) at least one handle for driving said annular array of surgical staples from said staple carrying portion; and
 d) an anvil assembly positioned adjacent said staple carrying portion, said anvil assembly including:
  i) a shaft having mounting means at one end for mounting to said frame portion;
  ii) an anvil member mounted on said shaft at a second end of said shaft, said anvil member having a housing and an annular array of anvil cups disposed thereon for crimping said surgical staples; and
  iv) at least one channel extending over an outer surface of said housing and communicable with an interior thereof for aiding the passage of fluids and tissue between said housing interior and an exterior surface of said housing.

12. In a circular anastomosis surgical apparatus having a frame, a staple carrying part mounted on a distal end portion of said frame, at least one handle for driving an annular array of staples from said staple carrying part, and an anvil asembly for crimping said staples, the improvement comprising an elongated depression formed on an outer surface of the anvil assembly for directing fluids and tissue from an interior of said anvil assembly and between said outer surface of said anvil assembly and a surrounding tissue section to reduce suction therebetween.

13. The circular anastomosis surgical apparatus as recited in claim 12 wherein said elongated depression includes at least one hole passing through said anvil assembly surface and at least one groove on said anvil assembly outer surface, said at least one groove being associated with said at least one hole.

14. An anvil assembly for use with a surgical fastening device comprising:
 a) a shaft configured to be mounted to a surgical fastening device;
 b) an anvil member mounted to said shaft, said anvil member having a housing and an array of fastener clinching portions disposed thereon;
 c) a plurality of vent holes extending between an interior of said anvil member and an outer surface of said housing for venting of gaseous pressure and tissue debris from within said anvil member; and
 d) a plurality of longitudinally extending grooves formed on said outer surface of said housing and communicable with said vent holes.

\* \* \* \* \*